United States Patent [19]

Megyeri et al.

[11] Patent Number: 4,697,017

[45] Date of Patent: Sep. 29, 1987

[54] PROCESS FOR THE PREPARATION OF 2-BROMO-α-ERGOCRYPTINE

[75] Inventors: Gábor Megyeri; Tibor Keve; János Galambos; Lajos Kovács, Jr.; Béla Stefkó; Erik Bogsch; Ferenc Trischler, all of Budapest, Hungary

[73] Assignee: Richter Gedeon Vegyeszeti Gyar RT, Budapest, Hungary

[21] Appl. No.: 869,203

[22] Filed: May 30, 1986

[30] Foreign Application Priority Data

Jun. 12, 1985 [HU] Hungary ................................. 2300

[51] Int. Cl.$^4$ .......................................... C07D 519/02
[52] U.S. Cl. ................................... 544/346; 260/694; 546/67; 546/68; 546/69
[58] Field of Search ........................... 546/67, 68, 69; 544/346; 260/694

[56] References Cited

U.S. PATENT DOCUMENTS

| | | | |
|---|---|---|---|
| 3,752,814 | 8/1973 | Fluckiger et al. | 544/346 |
| 3,752,888 | 8/1973 | Fluckiger et al. | 544/346 |
| 4,348,391 | 9/1982 | Stütz et al. | 546/67 |
| 4,542,135 | 9/1985 | Kobel et al. | 544/346 |
| 4,609,731 | 9/1986 | Jurgec et al. | 544/346 |

FOREIGN PATENT DOCUMENTS

| | | | |
|---|---|---|---|
| 56358 | 7/1982 | European Pat. Off. | 546/68 |
| 2330912 | 1/1974 | Fed. Rep. of Germany | 514/288 |
| 573431 | 3/1976 | Switzerland | 546/69 |

OTHER PUBLICATIONS

Troxler et al, Helv. Chim. Acta. vol. 40, 2160 (1957).

*Primary Examiner*—Donald G. Daus
*Assistant Examiner*—Cecilia Shen
*Attorney, Agent, or Firm*—Karl F. Ross; Herbert Dubno

[57] ABSTRACT

The invention relates to a novel process for the preparation of 2-bromo-α-ergocryptine and its acid addition salt by brominating α-ergocryptine in such a way that the bromination is carried out at room temperature by using a dimethylsulphoxide-hydrogen bromide mixture containing no more 0.02% of water and, if desired, converting the thus-obtained 2-bromo-α-ergocryptine to an acid addition salt in a known manner.

2 Claims, No Drawings

PROCESS FOR THE PREPARATION OF 2-BROMO-α-ERGOCRYPTINE

The invention relates to a novel process for the preparation of 2-bromo-α-ergocryptine and its acid addition salts.

The derivatives brominated on the $C_2$ atom of the ergolene skeleton are known, therapeutically useful compounds. The most valuable of these compounds is 2-bromo-α-ergocryptine.

The secretion of the prolaction hormone and the somatotropic (growth) hormone is inhibited by 2-bromo-α-ergocryptine; thus, this compound is therapeutically used for the treatment of amenorrhoea and galactorrhoea as well as for the healing of macromegaly.

Different cancers, first above all the breast cancer where the activation and re-activation of prolaction play an important role, are preferably influenced by the prolactin-inhibiting 2-bromo-α-ergocryptine. The dopaminergic receptors of the central nervous system are stimulated and the Parkinson's disease can effectively be treated by this compound.

The $C_2$-bromination of ergolene derivatives was first time described by F. Troxler and A. Hofmann [Helv. Chim. Acta 40, 2160 (1957)]. These authors used N-bromosuccinimide for the bromination.

The preparation of 2-bromo-α-ergocryptine was first time described in the Swiss patent specification No. 507,249, according to which the compound was obtained by brominating α-ergocryptine. The bromination was carried out in an inert solvent by using a mild brominating agent such as N-bromophthalimide, N-bromosuccinimide, N-bromocaprolactam or a bromine-dioxane complex at a temperature between 10° C. and 80° C. As inert apolar solvent e.g. dioxane, acetonitrile or dichloromethane was used. The brominating reaction lasted from 70 minutes to 6 hours.

Although the brominating agent was used in a large excess, this reaction was neither selective nor quantitative. A great part of the starting substance was decomposed to give dark-coloured, unidentifiable, partially resinous products. The unchanged starting compound and the sideproducts were separated from the 2-bromo-α-ergocryptine by using column chromatography. No yield was given in this patent specification.

According to the German patent specification No. 2,752,532, α-ergocryptine was brominated under an inert gas, e.g. under nitrogen, by using pyrrolidine-hydrotribromide or N-bromosaccharine in the presence of a radical initiator, in a cyclic ether as solvent, at room temperature or at a moderately elevated temperature. From the crude reaction mixture, the product could only be isolated by column chromatography purification using a special adsorbent. The bromination was carried out between room temperature and 55° C. The reaction proceeded at 50° C. within 30 minutes, whereas the reaction mixture had to be kept for 2 days at room temperature for completion. Yield of 78 to 87% were given in the examples of this patent specification.

On reproducing the above-described process the indicated yields could not be verified during our experiments; namely, the α-ergocryptine used as starting substance was consumed during the reaction, however 20 to 30% of an unknown side-product and 5 to 10% of 2-bromo-α-ergocryptinine were formed in addition to the desired 2-bromo-α-ergocryptine. These substances could only be removed by using said special adsorbent in the above-mentioned column chromatography purification.

Summing up, a common disadvantage of the above-reported processes consists in that the disclosed reaction times are long and the product obtained must be purified by using column chromatography which can only be realized with high difficulties on industrial scale.

The aim of the invention is to find out a selective brominating agent attacking only on the $C_2$ atom of the ergolene skeleton, by using which the drawbacks of the processes of the prior art, e.g. the epimerization, formation of side-products and the thus-required purification by column chromatograhy, can be eliminiated.

According to the novel process of the present invention α-ergocryptine is brominated by using a system consisting of anhydrous dimethylsulphoxide and hydrogen bromide, at room temperature. As compared to the processes known until now, the brominating reaction of the invention proceeds within a much shorter time, i.e. within 10 to 15 minutes, and the crude reaction mixture does not contain any starting α-ergocryptine.

Surprisingly and unexpectedly it has been observed that neither the peptide moiety of the molecule is decomposed nor an epimerization occurs in the strongly acidic medium. The bromination occurs selectively at the $C_2$ atom of the ergolene skeleton.

It is important to carry out the bromination in an anhydrous system consisting of dimethylsulphoxide and hydrogen bromide. Namely, it has been observed during our experiments that the substitution of the aromatic hydrogen occurs most selectively when the water content of the mixture is below 0.02% by volume. The formation of undesired side-products is promoted by an increase in the water content.

An advantage of the process of the invention is resulted by the reaction conditions of the bromination. Namely, in the brominating processes known so far, the starting compound reacts in the form of a base. It is well-known that ergot alkaloids being present in the solution in the form of a base are epimerized under the effect of heat or storage, whereby the therapeutically inactive "inine" form also appears besides the starting alkaloid having the "in" form.

According to the process of the invention, the bromination is carried out with a salt form of the alkaloid, at room temperature. The salt form is built up in such a way that the tertiary nitrogen present in the ring D of the alkaloid to be brominated is protonated by the hydrogen bromide which is in an excess as calculated for the compound to be brominated and which forms the brominating agent with the dimethylsulfoxide. The epimerization is prevented by the stable salt form. As the bromination is not accompanied by epimerization at the $C_8$ atom of the ergolene skeleton and the physical properties of the formed side-product are significantly different from those of the aimed compound, the obtained 2-bromo-α-ergocryptine final product does not require a purificiation by using column chromatography, an isolation by crystallization is satisfactory.

Pure α-ergocryptine may be used as starting material for the process of the invention, however, the so-called crude alkaloid mixtures containing other ergot alkaloids or the salts of these mixtures can also be brominated by using this process.

The process of the invention is described in detail hereinafter.

The calculated amount of gaseous hydrogen bromide is absorbed in dry dimethylsulphoxide, whereupon the starting α-ergocryptine or a crude alkaloid mixture is dissolved in the obtained solution containing hydrogen bromide in dimethylsulphoxide.

The $C_2$-substitution of the ergolene skeleton is most advantageous when the hydrogen bromide content of the dimethylsulfoxide is about from 0.0003 to 0.0005 mole/ml and about 12 equivalents of hydrogen bromide are used for 1 mole of the compound to be brominated.

After 20 minutes, the reaction mixture is poured into a 5-fold amount of water and alkalinized to a pH value of 8 to 9 by adding a base preferably ammonium hydroxide. The precipitated 2-bromo-α-ergocryptine is filtered, washed and then purified by recrystallization from an ether-type organic solvent, preferably e.g. from diisoprophy ether.

On using a crude alkaloid mixture or its salt as starting material, the obtained 2-brominated ergot alkaloid mixture is isolated as a base according to the method described above whereupon 2-bromo-α-ergocryptine is separated from other accompanying 2-brominated alkaloid derivatives by using chromatography.

If desired, the 2-bromo-α-ergocryptine prepared by the process of the invention may be transformed into an acid addition salt. These acid addition salts can be prepared in any inert organic solvent such as methyl ethyl ketone by dissolving 2-bromo-α-ergocryptine in the above solvent and adding the appropriate acid or a solution of this acid in the above solvent until the pH value of the mixture becomes acidic. Then, the precipitated acid addition salt is separated from the mixture in any suitable manner, e.g. by filtration.

The process of the invention is illustrated in detail by the following non-limiting Examples.

EXAMPLE 1

Preparation of 2-bromo-α-ergocryptine

Dry gaseous hydrogen bromide is introduced to 70 ml. of anhydrous dimethylsulphoxide at room temperature. The amount of the introduced hydrogen bromide is measured by titrating against 0.1N sodium hydroxide solution. The hydrogen bromide is introduced until reaching a hydrogen bromide content of 0.0003 to 0.0005 mole/ml. in the dimethylsulphoxide. Then 10 g (0.01737 mole) of α-ergocryptine are dissolved in an amount containing 12 equivalents of hydrogen bromide as taken out from the thus-obtained mixture containing hydrogen bromide in dimethylsulphoxide. The reaction mixture is stirred at room temperature for 15 minutes beginning from the complete dissolution of α-ergocryptine, then poured in 5 volumes of water as calculated for the volume of dimethylsulphoxide. Then the mixture is alkalinized to a pH value of 8 to 9 by adding ammonium hydroxide, the precipitated 2-bromo-α-ergocryptine is filtered off, washed twice with 10 ml. of water each, dissolved in 200 ml. of dichloromethane and dried over anhydrous sodium sulphate. After filtering off the drying agent, 200 ml. of diisopropyl ether are added to the solution and dichloromethane is distilled off under atmospheric pressure. 2-bromo-αergocryptine separated from the distillation residue is filtered off and washed to give a yield of 8.4 g. (74%), m. p.: 215°–217° C., $[\alpha]_D^{20} = -190°$ c=1%, dichloromethane).

EXAMPLE 2

Preparation of 2-bromo-α-ergocryptine methanesulphonate 8.4 g. (0.01285 mole) of 2-bromo-α-ergocryptine are dissolved in 84 ml. of methyl ethyl ketone and to this solution 1.23 g. (molar equivalent) of methanesulphonic acid diluted with 5 ml. of methyl ethyl ketone are dropped under constant stirring. The crystallization immediately begins. After stirring for 20 minutes, the precipitated crystals are filtered off and washed three times with 20 ml. of methyl ethyl ketone each to give the title salt in a yield of 8.7 g. (90%), m.p.: 192°–196° C., $[\alpha]_D^{20} = +95°$ (c=1%, methanol/dichloromethane 1:1).

EXAMPLE 3

Preparation of 2-bromo-α-ergocryptine methanesulphonate (a) Bromination

Gaseous hydrogen bromide is introduced into 300 ml. of anhydrous dimethylsulphoxide up to a concentration of 0.3 to 0.5 mmole of hydrogen bromide 1 ml. of dimethylsulphoxide. The acid content of the solution can be determined by titrating against 0.1N sodium hydroxide solution in the presence of methyl red as indicator.

5.0 g. of a crude ergot alkaloid base mixture (beige amorphous powder, containing as an average 48% of α-ergocryptine and ergocryptinine and 25% of ergosine with a total alkaloid content of 79%) are dissolved in an amount of the hydrogen bromide-dimethylsulphoxide solution containing hydrogen bromide in a 12-fold molar excess as calculated for the average molecular weight of the total alkaloid content of the crude base mixture. The reaction mixture is stirred at room temperature for 20 minutes beginning from the dissolution of the starting material, then poured into 5 volumes of cold water as calculated for the volume of dimethylsulphoxide. The pH value of the solution is adjusted to 8 by adding 25% ammonium hydroxide solution, after staying for 1 hour the precipitate is filtered off and washed with cold water. The precipitate is dissolved in 100 ml. of dichloromethane, dried over anhydrous sodium sulphate and then evaporated under reduced pressure.

The dry residue is dissolved in 50 ml. of dichloromethane containing 2% of ethanol and clarified by passing through an aluminum oxide bed with a thickness of 5 cm. The solution, made free from the tarry side-products, is completely evaporated under reduced pressure to give 2.22 g. of dry residue with an average content of 64% of 2-bromoα-ergocryptine and 2-bromo-α-ergocryptinine.

The conversion is 52% as calculated for the α-ergocryptine content of the crude ergot alkaloid base mixture.

(b) Epimerization

The dry residue obtained after clarifying is dissolved in a mixture containing 10 ml. of acetone, 1.20 ml. of methanol. 0.22 ml. of 85% phosphoric acid and 0.44 ml. of glacial acetic acid. The reaction mixture is heated at 55° C. for 3 hours while stirring, then 45 ml. of acetone are added to the mixture containing a precipitate which is thereafter set aside overnight at room temperature. After filtration the crystals are washed with acetone and dried to give 1.35 g. of a mixture containing 2-bromo-α-ergocryptine with bromoergosine as phosphate salts. The average 2-bromo-α-ergocryptine base content of this mixture is 74%.

The conversion amounts to 70% as calculated for the total 2-bromo-α-ergocryptine and 2-bromo-α-ergocryptinine content of the brominated base mixture.

The salt mixture is suspended in 30 ml. of dichloromethane and 30 ml. of water and the pH value of this mixture is adjusted to 8 by adding sodium hydrogen carbonate solution. After separation, the aqueous phase is extracted twice with 25 ml. of dichloromethane each, the combined organic layer is dried over anhydrous sodium sulphate and evaporated to dryness under reduced pressure.

(c) Separation

The dry residue is separated by using a column chromatographic method. As an adsorbent, a 100-fold amount of al minum oxide whereas as eluant ethyl acetate are used. The fractions containing pure 2-bromo-α-ergocryptine are evaporated under reduced pressure to give 0.88 g. of 2-bromo-α-ergocryptine.

The yield is 88% as calculated for the 2-bromo-α-ergocryptine content of the epimerized phosphate salt mixture.

The dry residue is dissolved in 10 ml. of absolute methyl ethyl ketone and the pH value of this solution is adjusted to 3.5 to 4.0 by adding methanesulphonic acid diluted to the 5-fold with methyl ethyl ketone. The crystalline precipitate is filtered off, washed with methyl ethyl ketone, then with diethyl ether and dried to give 0.81 g. of 2-bromo-α-ergocryptine methanesulphonate. Thus, the conversion of the salt formation is 80%.

The conversion of the whole process is 26% as calculated for the total amount of α-ergocryptine and α-ergocryptine and α-ergocryptinine measured (determined) in the starting crude base mixture.

EXAMPLE 4

Preparation of 2-bromo-α-ergocryptine methanesulphonate 5.0 g. of a crude phosphate salt mixture (a greyish-brown powder containing 37% of α-ergocryptine and 30% of ergosine with a total alkaloid content of 75%), prepared from acrude ergot alkaloid base mixture by epimerization according to the Example 3 b) and then by salt formation in a known manner, are dissolved in a solution containing dimethylsulphoxide and hydrogen bromide in an amount prepared and calculated as described in Example 3. The reaction mixture is stirred at room temperature for 20 minutes beginning from the dissolution, then worked up as described in Example 1 to give 1.94 g. of a dry residue containing 52% of 2-bromo-α-ergocryptine base as an average. The conversion is 48% as calculated for the α-ergocryptine content of the crude phosphate salt.

The chromatographic separation of the brominated base mixture and the salt formation are carried out as described in Example 3 to give 0.84 g. of 2-bromo-α-ergocryptine methanesulphonate. The conversion is 73% as calculated for the α-ergocryptine content of the brominated base mixture.

The overall conversion of the process is 38% as calculated for the α-ergocryptine content of the crude phosphate mixture.

We claim:

1. A process for the preparation of 2-bromo-α-ergocryptine and its acid addition salts by brominating α-ergocryptine, which comprises carrying out the bromination at room temperature by using a dimethylsulphoxide-hydrogen bromide mixture containing no more than 0.02% of water and, if desired, converting the thus-obtained 2-bromo-α-ergocryptine to an acid addition salt by using a method known per se.

2. A process as claimed in claim 1, which comprises using a crude ergot alkaloid base mixture or a salt thereof as staring material.

* * * * *